United States Patent [19]
Levie et al.

[11] Patent Number: 5,970,783
[45] Date of Patent: Oct. 26, 1999

[54] PULP CHIP FISSURE TEST DEVICE AND METHOD FOR ESTIMATING SCREENED PULP YIELD

[75] Inventors: Benjamin E. Levie, Mercer Island; Gail E. Johnson, Auburn; Gevan R. Marrs, Puyallup, all of Wash.

[73] Assignee: Weyerhaeuser Company, Tacoma, Wash.

[21] Appl. No.: 09/253,168

[22] Filed: Feb. 20, 1999

Related U.S. Application Data

[60] Provisional application No. 60/075,288, Feb. 19, 1998.

[51] Int. Cl.$^6$ .................................................... G01N 5/02
[52] U.S. Cl. ................................. 73/73; 73/53.03
[58] Field of Search ........................ 73/73, 53.03, 866, 73/436, 437; 162/49, 263; 177/50

[56] References Cited

U.S. PATENT DOCUMENTS

| | | | |
|---|---|---|---|
| 3,246,524 | 4/1966 | Shiba | 73/435 |
| 4,487,323 | 12/1984 | Marrs | 209/546 |

*Primary Examiner*—Hezron Williams
*Assistant Examiner*—Thuy Vinh Tran

[57] ABSTRACT

The invention consists of a method and apparatus for estimating screened pulp yield using water uptake rate of a sample of screened pulp chips. A dried chip sample is placed in a wire basket and totally immersed in water. A balance records the rate of water uptake over a period of about 35 seconds. This is preferably entered directly into a computer to give an output closely predicting the yield of screened pulp.

8 Claims, 2 Drawing Sheets

PULP CHIP FISSURE TEST DEVICE AND METHOD FOR ESTIMATING SCREENED PULP YIELD

This application claims benefit of Provisional Application Ser. No. 60/075,288, filed Feb. 19, 1998.

The present invention is directed to a method and apparatus for determining the extent of fissures or cracks in wood chips intended for use in the manufacture of wood pulp. The method is based on determination of liquid absorption rate and is of particular value as a quality control tool for chip properties.

BACKGROUND OF THE INVENTION

In order to improve pulping liquor penetration and avoid production of uncooked "knots", pulp chips are commonly screened and the overthick chips removed. The overthick chips may then be sliced to reduced thickness or they may be fed to compression rolls before they are returned into the digester fissures stream. Compression rolls partially crush the chips and open many surface cracks or fissures that allow more ready liquor penetration. The quality of sliced chips is easily monitored using conventional chip classification testing; e.g., as shown in Marrs U.S. Pat. No. 4,487,323. Compression rolls fissure the chips but do not significantly alter their size distribution. For this reason their quality is not easily monitored using conventional size classification methods. Up to the present time, compression roll effectiveness could only be monitored by pulping the chips and noting changes in pulp yield or other properties.

Screened yield is a direct function of how well chips absorb liquor. Where compression roll treated oversize chips are concerned, roll surface configuration and wear, nip settings, and effects of loading rates all affect chip absorbency characteristics. Thus, a fast and simple test method suitable for mill use that would readily and accurately indicate liquor absorbency properties would be of considerable value. The present invention is directed to that end.

SUMMARY OF THE INVENTION

The present invention is directed to a testing apparatus for rapid measurement of pulp chip liquid absorbency characteristics and to the method of its use. A measured quantity of oven dried chips is placed in an open mesh or otherwise foraminous basket. This is covered to retain the chips and completely submerged in water or other liquid. A balance continuously measures chip weight increase over time. By using experimental laboratory or plant results, a correlation algorithm between the rate of water takeup and screened pulp yield can be readily established. The balance output is preferably fed directly to a computer which will plot real time test results.

It is an object of the invention to provide a method for testing liquid absorption rate of wood chips for use in wood pulp production.

It is a further object to provide apparatus for accomplishing the above method.

These and many other objects will become readily apparent upon reading the following detailed description taken in conjunction with the drawings.

DETAILED DESCRIPTION OF THE PREFERRED EMBODIMENTS

Figure 1:
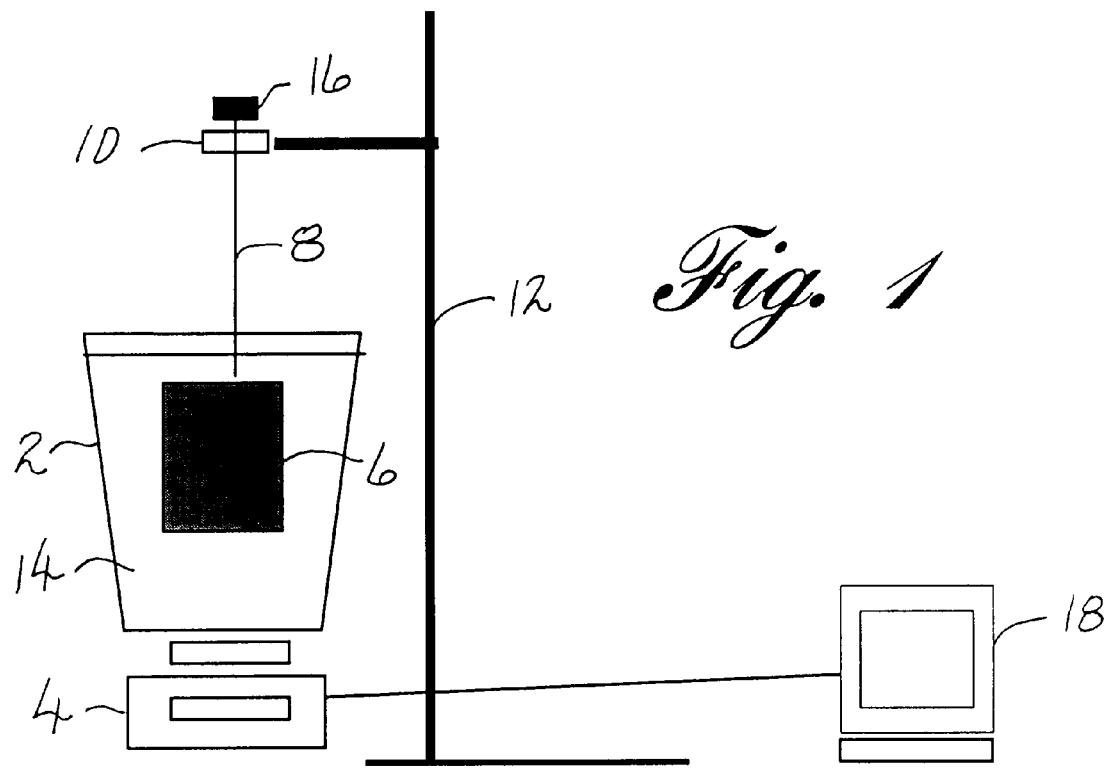
FIG. 1 is a schematic drawing of the chip fissure test apparatus.

Referring now to FIG. 1, a water container 2 is placed on balance 4. A chip sample is then placed in a covered wire mesh basket 6. The basket is suspended by rod 8 held by a clamp 10 on stand 12. At the beginning of the test the clamp is released and the basket is immersed by gravity under water 14 held in container 2. A stop 16 limits travel of the basket to a preset height above the bottom of the container. Clamp 10 is then immediately retightened. The balance directs readings continuously to a conventional personal computer 18 with software designed to give a readout of water absorption in terms calculated as milliliters water absorbed per kilogram of chips per minute (mL/kg/min).

The following parameters have been found useful for the apparatus. Balance 2 is a top loading electronic model with a 10,000 g capacity and a sensitivity of 0.1 g. The container is conventional and holds about 10 L of water Chips were classified into those within the 10–12 mm thickness category. It has been found that a narrow size range for the test sample is preferred in order to obtain the desired precision of the test. It should be noted that the apparatus is useful for measuring absorption rate of any size chip fraction except for pins and fines. A large sample of chips was dried in a 105° C. oven until they reached constant weight. A 300 g sample of the dry chips was placed in the wire mesh basket, covered, and fully immersed in the water container. Care was taken so that the chip basket did not contact the sides or bottom of the container. Weights were recorded every second for 35 seconds and rate of water absorption for the first 30 seconds after balance stabilization (usually 2–3 seconds) is determined by the computer software. From 5–10 replicate determinations were run from every chip batch.

Figure 2:
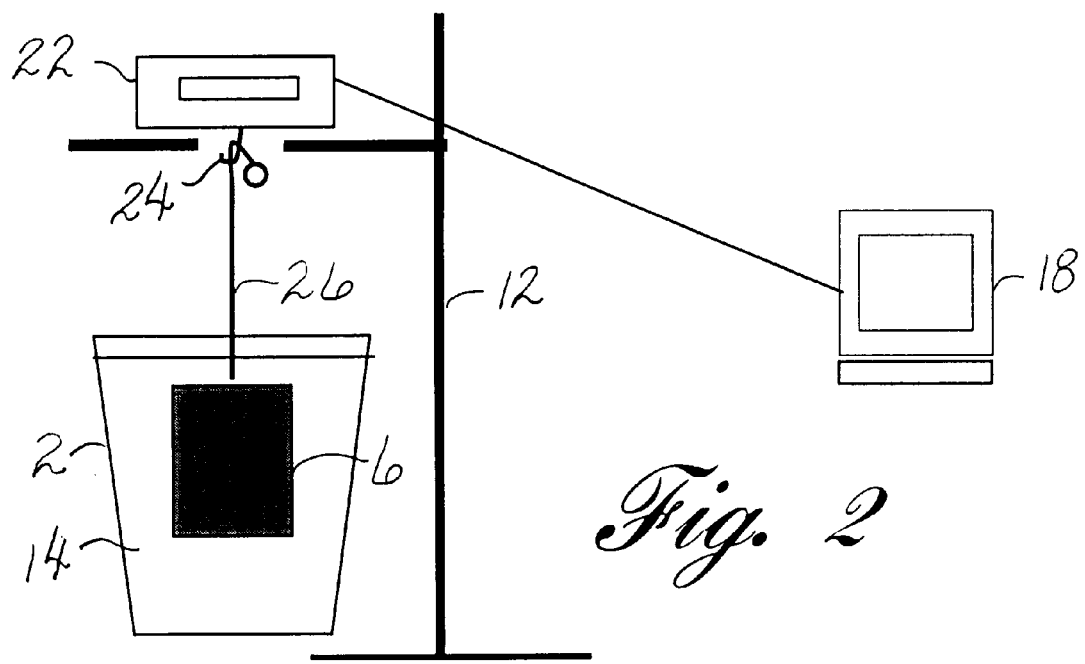
FIG. 2 is a schematic drawing of another embodiment of the apparatus.

FIG. 2 shows a variant of the method in which a lower capacity top loading balance with a range of about 1000 g, may be used. The balance 22 is placed atop a stand 20. Chip basket 6 is suspended from hook 24 depending from the balance by a suitable cord or flexible wire 26 and dropped into water bucket 2, again without contacting the sides or bottom. A stop, not shown, on string 26 limits travel of the chip basket.

In the method of FIG. 1, the weight of water absorbed by the chips is subtracted from the weight of water in the container, as recorded by the balance. In the method of FIG. 2, the weight of water absorbed by the chips is indicated as a weight increase of the foraminous container and chip sample.

Figure 3:
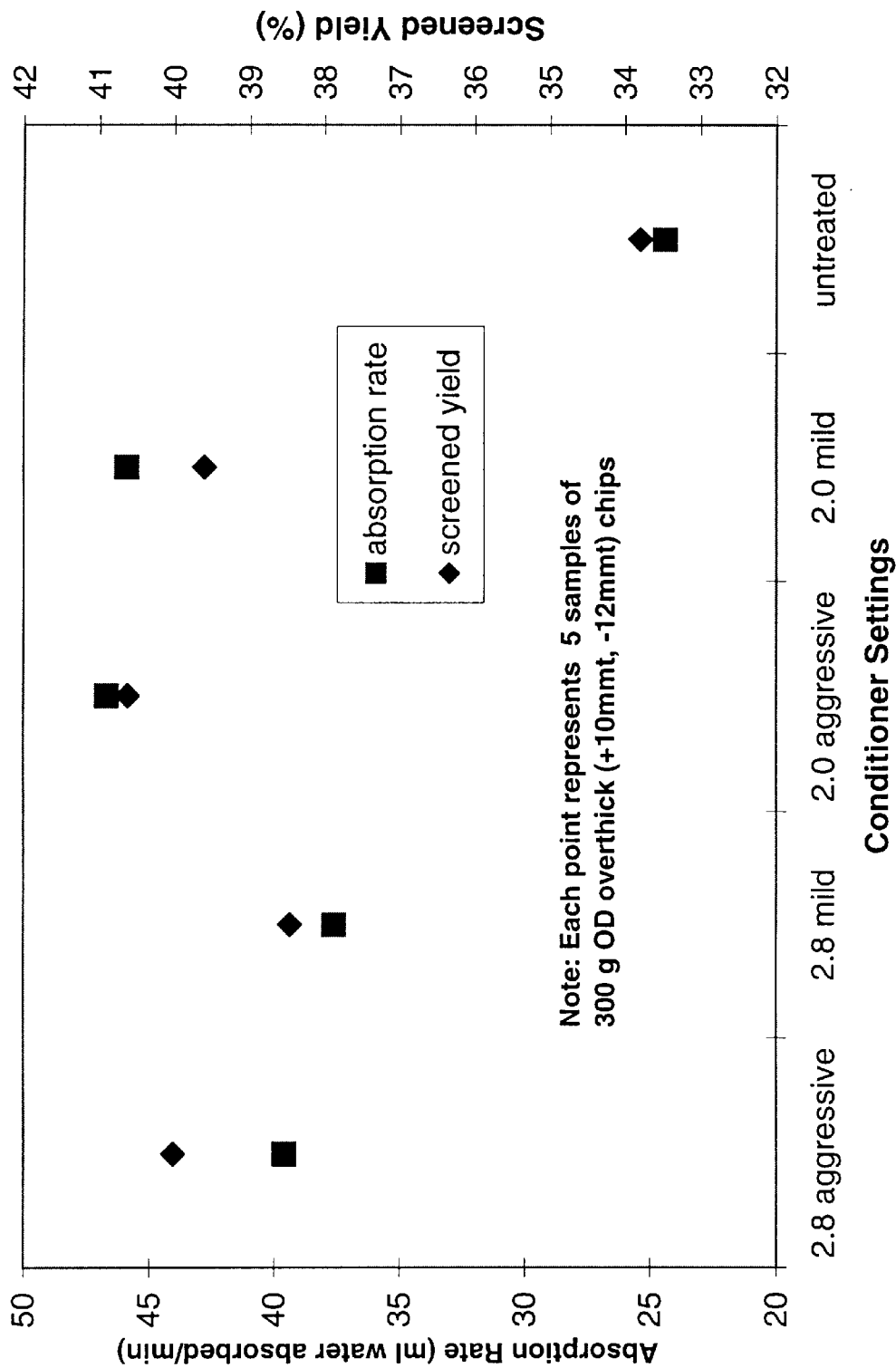
FIG. 3 is a comparison of fissure test results (measured as absorption rate) with pulping yields.

Correlation of results obtained with the absorption tester and actual pulping results has been excellent. FIG. 3 shows results from trials on oversize chips that were passed through different nip openings and different roll patterns on a Rader conditioner. Nip openings were 2.0 mm and 2.8 mm. The "old" or more aggressive pattern has a raised profile and the "new" or mild pattern has a reduced diamond profile on the rolls. Pulping results are expressed as screened yield and are shown on the graph with the reference axis being at the right side of the graph. Water absorption rate is plotted relative to the reference axis on the left side of the graph. The square points represent yields determined by laboratory pulping tests while the diamond shaped points show predicted yield from the water absorption rate. It is clear that there is a close correlation between screened pulp yield and chip absorbency.

As was noted earlier, the method is valuable for characterizing chips of any dimensions. It can help resolve differences that are not attributable to chip size but due to other factors that influence impregnation rates during pulping. The method, in conjunction with conventional analytical tests for cellulose, hemicellulose, and lignin, is expected to give a useful prediction of digester yield without the need for conducting laboratory pulping tests. A considerable saving in time and expense is thus realized.

EXAMPLE

The method was used successfully with oversize chips that had been passed through a roll-type conditioner at a Saskatchewan pulp mill. Test results of the conditioned chips showed decreased absorption indicating decreased fissuring. This suggested that the roll nip setting was excessive despite the belief that the nip had been set at a smaller gap. After the fissure test results became available, the mill staff investigated and found that the nip setting has been inadvertently increased, as the test had detected. Thus, the test may be used as an indicator of chip compression roll efficiency.

It will be readily apparent that many variations in the method can be made that have not been exemplified but will fall within the purview of the invention. This the invention should be considered limited only as it is defined in the following claims.

We claim:

1. A method of estimating screened yield of pulp wood chips which comprises:
   providing a sample of the chips within a foraminous enclosure;
   completely submerging the enclosure and chips in water;
   measuring the weight increase in the chips as a function of time to determine an absorption rate; and
   providing an algorithm correlating absorption rate with screened pulp yield; and
   estimating screened pulp yield by entering the rate of weight increase into the algorithm.

2. The method of claim 1 in which the chips are oven dried prior to the test.

3. The method of claim 1 including an electronic balance coupled to a computer to determine rate of weight increase and estimate pulp yield.

4. The method of claim 3 in which the foraminous enclosure is suspended from the balance while submerged in water.

5. The method of claim 3 in which the water is contained within a container and the container is located on a balance.

6. The method of claim I where the absorption rate may be used to indicate chip compression roll efficiency.

7. Apparatus for estimating the screened yield of pulp chips which comprises:
   a foraminous enclosure to contain a chip sample;
   a liquid container of greater dimensions than the foraminous enclosure;
   means to lower the foraminous enclosure into the liquid container without contacting the walls of the container;
   a balance operatively connected to the foraminous enclosure; and
   means to convert the balance output to an estimated pulp yield,
   whereby when a chip sample is placed within the foraminous enclosure and the enclosure is fully immersed in a liquid in the container, the balance will provide an output corresponding to the rate of weight increase of the chip sample, said output being convertible to an estimated screened pulp yield.

8. Apparatus for estimating the screened yield of pulp chips which comprises:
   a foraminous enclosure to contain a chip sample;
   a liquid container of greater dimensions than the foraminous enclosure;
   means to suspend the foraminous enclosure in the liquid container without the enclosure contacting the walls of the container;
   a balance operatively associated with the liquid container to indicate its weight; and
   means to convert the balance output to an estimated pulp yield,
   whereby when a chip sample is placed within the foraminous enclosure and the enclosure is fully immersed in a liquid in the container, the balance will provide an output corresponding to the rate of weight increase of the chip sample, said output being convertible to an estimated screened pulp yield.

* * * * *